United States Patent
Qian et al.

(10) Patent No.: US 12,234,234 B2
(45) Date of Patent: Feb. 25, 2025

(54) METHOD FOR SYNTHESIZING 1,7-NAPHTHYRIDINE DERIVATIVES

(71) Applicant: ChengDa PharmaCeuticals Co., Ltd., Zhejiang (CN)

(72) Inventors: Wei Qian, Zhejiang (CN); Yuhua Shi, Shanghai (CN); Xing Huang, Zhejiang (CN); Changming Dong, Guizhou (CN); Junkui Dang, Gansu (CN); Zhipeng Wang, Hainan (CN); Yu Feng, Sichuan (CN); Hong Xu, Zhejiang (CN); Zongxi Huang, Anhui (CN); Ye Chen, Zhejiang (CN); Huafei Shen, Zhejiang (CN); Jun Zhang, Anhui (CN)

(73) Assignee: ChengDa Pharmaceuticals Co., Ltd., Zhejiang (CN)

( * ) Notice: Subject to any disclaimer, the term of this patent is extended or adjusted under 35 U.S.C. 154(b) by 724 days.

(21) Appl. No.: 17/610,106

(22) PCT Filed: Nov. 17, 2020

(86) PCT No.: PCT/CN2020/129254
§ 371 (c)(1),
(2) Date: Nov. 9, 2021

(87) PCT Pub. No.: WO2021/120953
PCT Pub. Date: Jun. 24, 2021

(65) Prior Publication Data
US 2022/0235044 A1    Jul. 28, 2022

(30) Foreign Application Priority Data
Dec. 16, 2019 (CN) .......................... 201911296069.2

(51) Int. Cl.
*C07D 471/04* (2006.01)

(52) U.S. Cl.
CPC .................................. *C07D 471/04* (2013.01)

(58) Field of Classification Search
CPC .................................................... C07D 471/04
See application file for complete search history.

(56) References Cited

U.S. PATENT DOCUMENTS

| 9,133,174 B2 * | 9/2015 | Murakata ............. C07D 405/14 |
| 2014/0213581 A1 | 7/2014 | White et al. |
| 2015/0038497 A1 | 2/2015 | Lewis et al. |
| 2017/0174679 A1 | 6/2017 | Lajkiewicz et al. |
| 2018/0177784 A1 | 6/2018 | Wu et al. |

FOREIGN PATENT DOCUMENTS

| CN | 101501032 | * | 8/2009 |
| CN | 101501034 A | | 8/2009 |
| CN | 108699001 A | | 10/2018 |
| WO | WO201354291 | | 4/2013 |
| WO | WO2014138484 | | 9/2014 |

* cited by examiner

*Primary Examiner* — D Margaret M Seaman
(74) *Attorney, Agent, or Firm* — JEEN IP LAW, LLC

(57) ABSTRACT

The invention discloses a method for synthesizing 1,7-naphthyridine derivatives, which relates to the technical field of synthesizing pharmaceutical intermediates and organic chemical intermediates, wherein the method includes: (1) 2-chloro-3-amino-pyridine being used as Compound I as a starting material, and protecting an amino group to prepare Compound II; (2) the Compound II reacting with an aldehydation reagent under alkaline conditions to obtain Compound III; (3) cyclizing the Compound III with acrylate compounds under the action of Lewis acid to prepare compound IV.

13 Claims, No Drawings

METHOD FOR SYNTHESIZING 1,7-NAPHTHYRIDINE DERIVATIVES

TECHNICAL FIELD OF THE INVENTION

The invention relates to the technical field of synthesizing pharmaceutical intermediates and organic chemical intermediates, in particular to a method for synthesizing 1,7-naphthyridine derivatives.

DESCRIPTION OF THE PRIOR ART 1,7-Naphthyridine is an important pharmaceutical intermediates, and used very broadly, for example 1,7-Naphthyridine is used in type 4 phosphodiesterase (PDE4) inhibitors at Novartis AG, p38 mitogen-activated protein kinase inhibitors (CN101501034A) and dihydroorotate dehydrogenase (DHODH) inhibitors (J. Med. Chem. 2018, 61, 5162) at Spanish Omiero Laboratory and so on.

8-Chloro-1,7-naphthyridine-3-formic acid and its ester compounds are an important derived type of 1,7-naphthyridine compounds, and are necessary for some derivatives occurring at the 8- and 3-positions of the 1,7-naphthyridine skeleton. Recently, Some patents reported a series of new immunomodulatory active compounds (CN108699001A, US20170174679), which can be potentially used for treatment, prevention and improvement on certain cancers and infectious diseases. In the above-mentioned patents, many candidate drugs have 1,7-naphthyridine ring serving as a main mother nucleus structure. 8-Chloro-1,7-naphthyridine-3-formic acid and its ester compounds could be intermediates in the synthesis of drugs.

The difficulty in the synthesis of 8-Chloro-1,7-naphthyridine-3-formic acid and its ester dwells in the formation of the 1,7-naphthyridine ring structure. There are usually two ways for the synthesis, which are summarized as follows:

In one of the ways for the synthesis, WO201354291, US20170174679 and US2018177784 and other patents disclosed that 5-bromo-3-methylpyridine-2-carboxylate was used as a raw material to produce the target product by amino-ester exchange, imidization, cyclization, chlorination and coupling. The raw materials are expensive, and the coupling reaction catalyzed by palladium has very high costs.

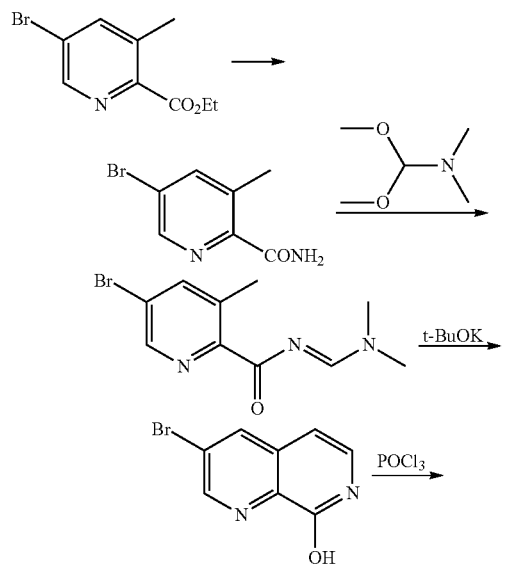

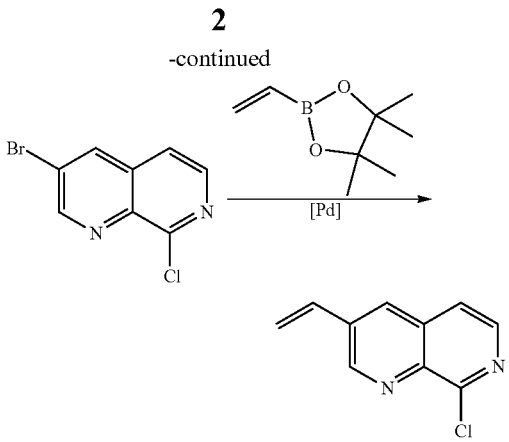

In another way for the synthesis, US2014213581, US20150038497, WO2014138484 disclosed that 2-cyano-3-bromo-5-chloropyridine was used as a raw material to prepare 8-chloro-3-cyano-1,7-naphthyridine by coupling, and adding, hydrolysis, cyclization, cyano substitution and chlorination. The coupling reaction catalyzed by palladium has very high cost, and the coupling and addition reactions involve a pressure reaction, which requires specialized equipments. In addition, the synthesis involves use of highly toxic products such as zinc cyanide, which can be dangerous, making it not suitable for industrial production.

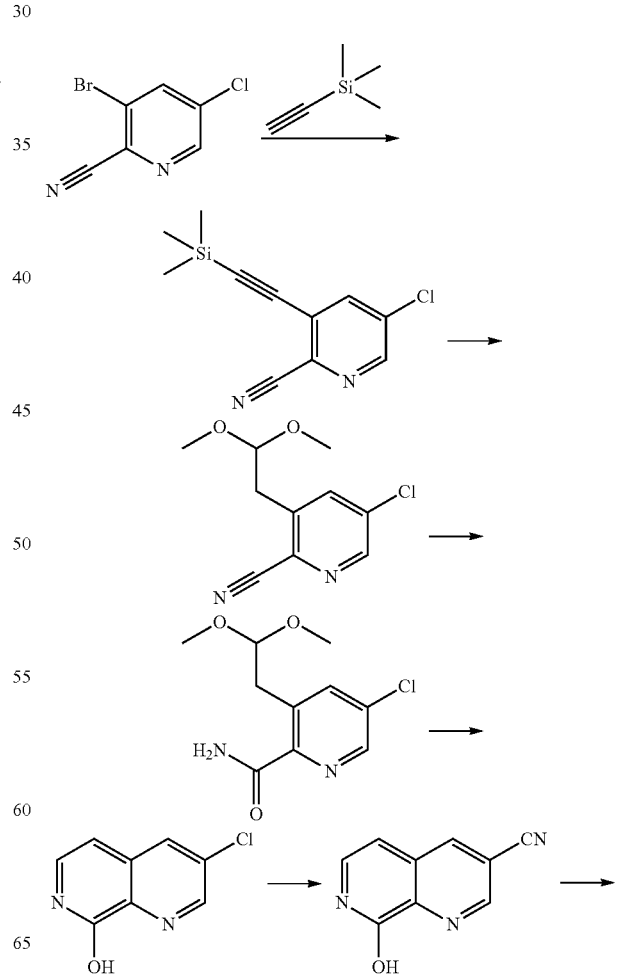

-continued

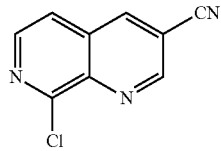

The existing ways of synthesis all have shortcomings, such as requiring complex steps, expensive reagents and catalysts, involving flammable, explosive, and highly toxic reagents and production processes, and causing severe environmental pollution. Therefore they are not conducive to large-scale industrial production.

In summary, in order to solve the shortcomings of the existing ways of synthesizing 1,7-naphthyridine derivatives, the present invention provides an easily-operated and high-yield method for synthesizing 1,7-naphthyridine derivatives.

SUMMARY OF THE INVENTION

The present invention provides a high-yield, high-quality and easily-operated method for synthesizing 1,7-naphthyridine derivatives suitable for industrial production with readily available raw materials.

The invention provides a method for synthesizing 1,7-naphthyridine derivatives, comprising the following steps:

(1) 2-chloro-3-amino-pyridine being used as Compound I that is a starting material, and protecting an amino group to prepare Compound II, wherein the Compound I, a protecting group reagent and an acid-binding agent are dissolved in a solvent at a reaction temperature of 20-150° C. After post-treatment, the Compound II is obtained. The molar ratio of the Compound I, the protecting group reagent and the acid-binding agent is 1.0:1.0~10.0:0~15.0, the protecting group reagent can be any one or more of di-tert-butyl dicarbonate, diisobnate, di-n-butyl dicarbonate, dibenzyl dicarbonate, diethyl dicarbonate, dimethyl dicarboutyl dicarbonate, di-n-propyl dicarbonate, diisopropyl dicarbonate, tert-butyl chloroformate, isobutyl chloroformate, n-butyl chloroformate, benzyl chloroformate, methyl chloroformate, ethyl chloroformate, n-propyl chloroformate and isopropyl chloroformate, the corresponding protective group R1 can be any one or more of tert-butoxycarbonyl, isobutoxycarbonyl, n-butoxycarbonyl, benzyloxycarbonyl, methoxycarbonyl, ethoxycarbonyl, n-propoxycarbonyl and isopropoxycarbonyl, the acid-binding agent is any one or more of sodium hydroxide, potassium hydroxide, potassium carbonate, sodium carbonate, triethylamine and N-methylmorpholine;

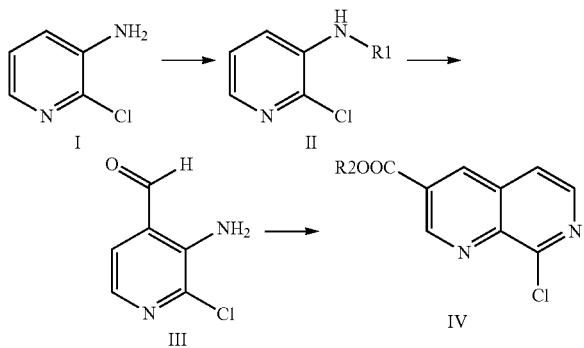

(2) the Compound II reacting with an aldehydation reagent under alkaline conditions to obtain Compound III, wherein after the Compound II, alkali, tetramethylethylene diamine and solvent react at −100~−10° C., the aldehydation reagent is added dropwise, and an aldehydation reaction is carried out at −100~−10° C.; after post-treatment, the Compound III is obtained; the molar ratio of the Compound II, the alkali, the tetramethylethylene diamine and the aldehydation reagent is 1.0:1.0~5.0:1.0~5.0:1.0~5.0; the alkali can be any one or more of n-butyl lithium, tert-butyl lithium, lithium diisopropylamide, and lithium hexamethyldisilazide, the solvent can be any one or more of tetrahydrofuran, methyltetrahydrofuran, dioxane, and methyl tert-butyl ether, the aldehydation reagent is any one or more of dimethylformamide, diethylformamide, and N-formylmorpholine;

(3) cyclizing the Compound III with acrylate compounds under the action of Lewis acid to prepare Compound IV, wherein the Compound III, the Lewis acid and the acrylate compounds are dissolved in a solvent, and a cyclization reaction occurs at 10~120° C. to prepare the Compound IV; the solvent can be any one or more of ethyl acetate, isopropyl acetate, acetonitrile, tetrahydrofuran, methyltetrahydrofuran, dioxane and methyl tert-butyl ether; the Lewis acid can be any one or more of sodium tetrafluoroborate, lithium tetrafluoroborate, calcium tetrafluoroborate and potassium tetrafluoroborate, the acrylate compounds are N,N-dimethylamino ethyl acrylate, N,N-dimethylamino acrylate, N,N-dimethylamino propyl acrylate and N,N-dimethylamino butyl acrylate; the molar ratio of the Compound III, the Lewis acid and the acrylate compounds is 1.0:0.5~10: 1.0~5.0, preferably 1.0:1.0~2.0:1.5~3.0, R2 in the Compound IV can be any one of a hydrogen atom, a methyl group, an ethyl group, a propyl group, an isopropyl group, a butyl group, an isobutyl group and a tert-butyl group.

As a further improvement of this solution, in step (1), the reaction temperature can be 60~100° C.

As a further improvement of this solution, in step (1), the protecting group reagent can be any one or more of tert-butyl chloroformate, isobutyl chloroformate, di-tert-butyl dicarbonate and diisobutyl decarbonate, preferably tert-Butoxycarbonyl and isobutoxycarbonyl.

As a further improvement of this solution, in step (1), the solvent can be any one or more of toluene, tetrahydrofuran, methyltetrahydrofuran, dioxane, methyl tert-butyl ether and n-heptane, preferably methyltetrahydrofuran and/or dioxane.

As a further improvement of this solution, in step (1), the acid-binding agent can be potassium carbonate, sodium carbonate and triethylamine.

As a further improvement of this solution, in step (1), the molar ratio of the Compound I, the protecting group reagent and the acid-binding agent can be 1.0:1.0~2.0:0~3.0.

As a further improvement of this solution, in step (2), after the Compound II, the alkali, the tetramethylethylene diamine and the solvent react at −20~−40° C., the aldehydation reagent can be added dropwise, and an aldehydation reaction can be carried out at −20~−40° C.; after post-treatment, the Compound III can be obtained.

As a further improvement of this solution, in step (2), the alkali is n-butyl lithium, the solvent can be tetrahydrofuran, the aldehydation reagent is N-formylmorpholine; the molar ratio of the Compound II, the alkali, the tetramethylethylene diamine and the aldehydation reagent can be 1.0:2.0~3.0:1.0~2.0:1.0~2.0.

As a further improvement of this solution, in step (3), the Compound III, the Lewis acid and the acrylate compounds are dissolved in a solvent, and a cyclization reaction occurs at 50~80° C. to prepare the Compound IV.

As a further improvement of this solution, in step (3), the solvent is acetonitrile, the Lewis acid can be lithium tetrafluoroborate, the acrylate compounds are N,N-dimethylamino ethyl acrylate, the molar ratio of the Compound III, the Lewis acid and the acrylate compounds can be 1.0:1.0~2.0:1.5~3.0, R2 in the Compound IV is an ethyl group.

Compared with the prior art, the method for synthesizing 1,7-naphthyridine derivative according to the invention has the following advantages:

(1) The technical solution of the invention is relatively simple and are commercially available and uses relatively cheap raw materials without complex, special operation, making it suitable for industrial production.
(2) The pharmaceutical intermediates prepared therein have higher yield and better quality.

DETAILED DESCRIPTION OF THE INVENTION

In order to make the objectives, technical solutions, and advantages of the invention clearer, the invention will be further described in conjunction with embodiments as follows:

Example 1

The synthesis reaction equation is illustrated as follows:

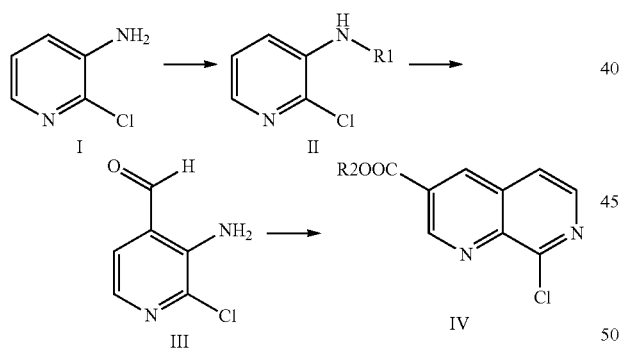

Step (1) Preparing Compound II

Under a nitrogen atmosphere, add 50.0 g of 2-chloro-3-amino-pyridine (I) (0.39 mol, 1.0 eq), 135.8 g of di-tert-butyl dicarbonate (0.63 mol, 1.6 eq) and 150 g of 1,4-dioxane into a reaction flask, then stir until they are completely dissolved, raise the temperature to 80° C. and stir them to react, and keep controlling them to be tested during reaction until the raw materials completely react. After that, add saturated salt water for washing twice, then distil the organic layer under reduced pressure to no cut fraction, add n-heptane for beating to obtain 71.1 g of a faint yellow solid (yield 80%) after filtration, which produces Compound II. The nuclear magnetic data is as follows: $^1$H NMR (400 MHz, Chloroform-d) δ 9.98 (s, 1H), δ8.37 (d, 1H), δ7.66 (d, 1H), δ6.98 (s, 1H), δ1.53 (s, 9H).

Step (2) Preparing Compound III

Under a nitrogen atmosphere, add 50.0 g of the Compound II (0.22 mol, 1.0 eq), 38.1 g of tetramethylethylene diamine (0.33 mol, 1.5 eq) and 200 g of tetrahydrofuran into a reaction flask, completely dissolving the material through stirring, lower the temperature to −40~−30° C., and dropwise add 127.4 g of n-butyl lithium n-hexane solution (0.47 mol, 2.4 eq), preserve heat and keep reacting for 2 h; after finishing heat preservation, lower the temperature to −40° C., then add 34.5 g of N-formylmorpholine (0.3 mol, 2.0 eq), and stir the mixture for 30 minutes. After finishing reaction, control the temperature to 0-20° C., then adjust the pH value to 5-7 with 3M hydrochloric acid, on layering, add 200 g of tetrahydrofuran to the aqueous phase to extract the organic phases once, then combine them; keep concentrating the organic liquid under reduced pressure until a large amount of solids precipitate, and add 300 g of n-heptane and evaporate the mixture with a cover to a certain volume; finally obtain 23.9 g of a yellow solid (yield 70%) after beating and filtration to produce Compound III. The nuclear magnetic data is as follows: $^1$H NMR (400 MHz, Chloroform-d) δ9.96 (s, 1H), δ7.86 (d, 1H), δ7.35 (d, 1H), δ6.54 (brs, 2H).

Step (3) Preparing Compound IV

Under a nitrogen atmosphere, add 50.0 g of the Compound III (0.32 mol, 1.0 eq), 45.0 g of lithium tetrafluoroborate (0.48 mol, 1.5 eq), 59.4 g of N,N-dimethylamino ethyl acrylate (0.42 mol, 1.3 eq) and 300.0 g of acetonitrile into a reaction flask, raise the temperature to 80° C. until reacting; after finishing reaction, concentrate the liquids under reduced pressure to dryness, add ethyl acetate to dissolve the solid, and then wash the mixture twice with water, concentrate the organic layer under reduced pressure to a certain volume, finally obtain 54.4 g of a yellow solid (yield 72%) after beating and filtration, to produce Compound IV. The nuclear magnetic data is as follows: $^1$H NMR (400 MHz, DMSO-$d_6$): δ9.41 (s, 1H), δ9.05 (d, 1H), δ8.48 (d, 1H), δ8.13 (d, 1H), δ4.44 (q, 2H), δ1.40 (t, 3H); $^{13}$C NMR (400 MHz, DMSO-$d_6$): δ164.2, 152.4, 152.1, 143.5, 140.9, 138.5, 132.5, 127.7, 122.5, 62.3, 14.5. The mass spectrum data is as follows: LC-MS measured value: 237, calculated value: [M+H]237.

Example 2

The synthesis reaction equation is as follows:

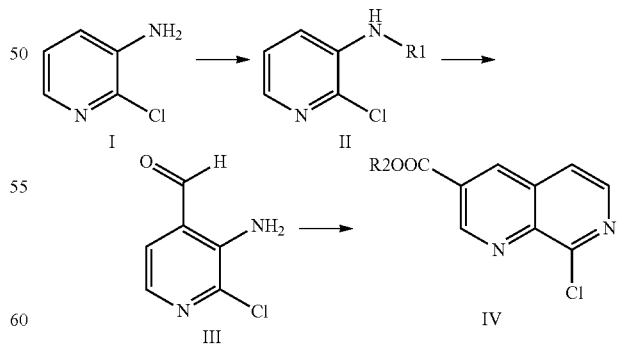

Step (1) Preparing Compound II

Add 50.0 g of 2-chloro-3-amino-pyridine (I) (0.39 mol, 1.0 eq), 47.2 g of triethylamine (0.47 mol, 1.2 eq) and 175 g of methyltetrahydrofuran into a reaction flask, and stir them to be completely dissolved, dropwise add 80.8 g of tert-butyl chloroformate (0.59 mol, 1.5 eq) at the controlled temperature of 60° C.; stir them while they are reacting for 3 h, and keep controlling them to be tested during reaction. After the raw materials completely react, distill the liquids under reduced pressure to no cut fraction, add n-heptane, then wash them twice with saturated sodium bicarbonate, next distill and concentrate the liquids under reduced pressure to a certain volume; finally obtain 75.6 g of a white solid (yield 85%) after cooling-crystallization and filtration, to produce Compound II. The nuclear magnetic data is as follows: $^1$H NMR (400 MHz, Chloroform-d) δ9.98 (s, 1H), δ8.37 (d, 1H), δ7.66 (d, 1H), δ6.98 (s, 1H), δ1.53 (s, 9H).

Step (2) Preparing Compound III

Under a nitrogen atmosphere, add 50.0 g of the Compound II (0.22 mol, 1.0 eq), 38.1 g of tetramethylethylene diamine (0.33 mol, 1.5 eq) and 300 g of methyl tert-butyl ether into a reaction flask; after stirring and completely dissolving them, lower the temperature to −30~−20° C., and dropwise add 143.0 g of n-butyl lithium n-hexane solution (0.52 mol, 2.4 eq); preserve heat and keep reacting for 2 h, after finishing heat preservation, lower the temperature to −40° C., then add 32.0 g of N-formylmorpholine (0.44 mol, 2.0 eq), and stir the mixture for 30 min. After finishing reaction, control the temperature to 0-20° C., then adjust the pH value to 5-7 with 3M hydrochloric acid, on layering, add 300 g of methyl tert-butyl ether to the aqueous phase to extract the organic phases twice, then combine them; keep concentrating the organic liquid under reduced pressure until a large amount of solids precipitate, and add 300 g of n-heptane and evaporate the mixture with a cover to a certain volume; finally obtain 24.9 g of a yellow solid (yield 73%) after beating and filtration, to produce Compound III. The nuclear magnetic data is as follows: $^1$H NMR (400 MHz, Chloroform-d) δ9.96 (s, 1H), δ7.86 (d, 1H), δ7.35 (d, 1H), δ6.54 (brs, 2H).

Step (3) Preparing Compound IV

Under a nitrogen atmosphere, add 50.0 g of the Compound III (0.32 mol, 1.0 eq), 24.0 g of lithium tetrafluoroborate (0.26 mol, 0.8 eq), 59.6 g of N,N-dimethylamino ethyl acrylate (0.42 mol, 1.3 eq) and 300.0 g of acetonitrile into a reaction flask, preserve heat while reacting at 80° C., after finishing reaction, concentrate the liquids under reduced pressure to dryness, add ethyl acetate to dissolve the solids, and then wash the mixture twice with water; concentrate the organic layer under reduced pressure to a certain volume; finally obtain 49.9 g of a yellow solid (yield 66%) after beating and filtration, to produce Compound IV. The nuclear magnetic data is as follows: 1H NMR (400 MHz, DMSO-d$_6$): δ9.41 (s, 1H), δ9.05 (d, 1H), δ8.48 (d, 1H), δ8.13 (d, 1H), δ4.44 (q, 2H), δ1.40 (t, 3H); 13C NMR (400 MHz, DMSO-d$_6$): δ164.2, 152.4, 152.1, 143.5, 140.9, 138.5, 132.5, 127.7, 122.5, 62.3, 14.5. The mass spectrum data is as follows: LC-MS measured value: 237, calculated value: [M+H]237.

Example 3

The synthesis reaction equation is as follows:

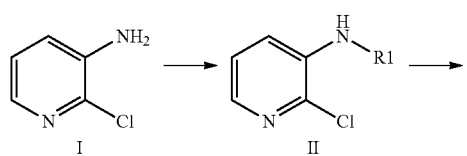

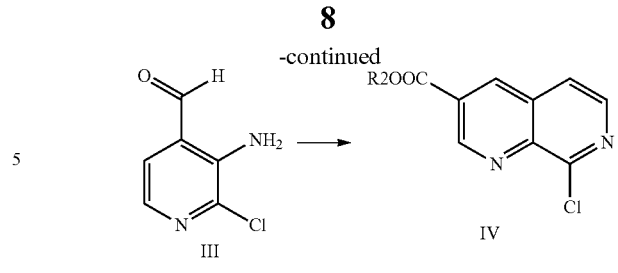

Step (1) Preparing Compound II

Add 50.00 g of 2-chloro-3-amino-pyridine (I) (0.39 mol, 1.0 eq), 61.8 g of sodium carbonate (0.58 mol, 1.5 eq) and 200 g of 1,4-dioxane into a reaction flask, and stir them, then slowly add 78.5 g of tert-butyl chloroformate (0.58 mol, 1.5 eq) at 60~70° C., and stir them while they react, keep controlling them to be tested during reaction. After the raw materials completely react, filter and desalinate the liquids, then distill the liquids under reduced pressure to no cut fraction, further add n-heptane to dissolve the solids, and wash them twice with saturated sodium bicarbonate, next distill and concentrate the liquids under reduced pressure to a certain volume; finally obtain 72.9 g of a white solid (yield 82%) after cooling-crystallization and filtration, which is the Compound II. The nuclear magnetic data is as follows: $^1$H NMR (400 MHz, Chloroform-d) δ 9.98 (s, 1H), δ8.37 (d, 1H), δ7.66 (d, 1H), δ6.98 (s, 1H), δ1.53 (s, 9H).

Step (2) Preparing Compound III

Under a nitrogen atmosphere, add 50.0 g of the Compound II (0.22 mol, 1.0 eq), 43.2 g of tetramethylethylene diamine (0.37 mol, 1.7 eq) and 200 g of 2-methyltetrahydrofuran into a reaction flask, after stirring and completely dissolving them; lower the temperature to −30~−20° C., and dropwise add 270 mL of lithium diisopropylamine tetrahydrofuran solution (0.53 mol, 2.4 eq); preserve heat and keep the reaction going for 2 h; after finishing heat preservation, lower the temperature to −40° C., then add 50.3 g of N-formylmorpholine (0.33 mol, 2.0 eq), and stir the mixture for 30 minutes. After finishing reaction, control the temperature to 0-20° C., then adjust the pH value to 5-7 with 3M hydrochloric acid, on layering, add 200 g of 2-methyltetrahydrofuran to the aqueous phase to extract the organic phases once, then combine them; keep concentrating the organic liquid under reduced pressure until a large amount of solids precipitate, and add 300 g of n-heptane and evaporate the mixture with a cover to a certain volume; finally obtain 23.3 g of a yellow solid (yield 68%) after beating and filtration, to obtain Compound III. The nuclear magnetic data is as follows: $^1$H NMR (400 MHz, Chloroform-d) δ9.96 (s, 1H), δ7.86 (d, 1H), δ7.35 (d, 1H), δ6.54 (brs, 2H).

Step (3) Preparing Compound IV

Under a nitrogen atmosphere, add 50.0 g of compound III (0.32 mol, 1.0 eq), 52.6 g of sodium tetrafluoroborate (0.48 mol, 1.5 eq), 59.4 g of N,N-dimethylamino ethyl acrylate (0.42 mol, 1.3 eq) and 300.0 g of acetonitrile into a reaction flask, raise the temperature to 80° C. until reacting; after finishing reaction, concentrate the liquids under reduced pressure to dryness, add ethyl acetate to dissolve the solids, and then wash the mixture twice with water, concentrate the organic layer under reduced pressure to a certain volume, finally obtain 51.4 g of a yellow solid (yield 68%) after beating and filtration, which is the Compound IV. The nuclear magnetic data is as follows: $^1$H NMR (400 MHz, DMSO-d$_6$): δ9.41 (s, 1H), δ9.05 (d, 1H), δ8.48 (d, 1H), δ8.13 (d, 1H), δ4.44 (q, 2H), δ1.40 (t, 3H); $^{13}$C NMR (400 MHz, DMSO-d$_6$): δ164.2, 152.4, 152.1, 143.5, 140.9, 138.5, 132.5, 127.7, 122.5, 62.3, 14.5. The mass spectrum data is as follows: LC-MS measured value: 237, calculated value: [M+H]237.

Compared with the prior art which has the disadvantages of causing severe environmental pollution, requiring expensive raw materials, and having complex synthesis process, the method for synthesizing 1,7-naphthyridine derivative according to the invention has the following advantages: (1) the technical solution of the present invention is relatively simple, using commercially available and relatively cheap raw materials without needing complex, special operations, making it suitable for industrial production; (2) the pharmaceutical intermediates prepared therein have higher yield and better quality.

The invention claimed is:

1. A method for synthesizing 1,7-naphthyridine derivatives, comprising the following steps:
   (1) dissolving Compound I, a protecting group reagent and an acid-binding agent in a solvent to make compound II at a reaction temperature of 20-150° C.;
   wherein the molar ratio of said Compound I, said protecting group reagent and said acid-binding agent is 1.0:1.0~10.0:0~15.0,
   wherein the compound I is a starting material and is 2-chloro-3-amino-pyridine;
   said protecting group reagent is any one or more of di-tert-butyl dicarbonate, diisobnate, di-n-butyl dicarbonate, dibenzyl dicarbonate, diethyl dicarbonate, dimethyl dicarboutyl dicarbonate, di-n-propyl dicarbonate, diisopropyl dicarbonate, tert-butyl chloroformate, isobutyl chloroformate, n-butyl chloroformate, benzyl chloroformate, methyl chloroformate, ethyl chloroformate, n-propyl chloroformate and isopropyl chloroformate,
   the corresponding protective group R1 in said compound II is any one or more of tert-butoxycarbonyl, isobutoxycarbonyl, n-butoxycarbonyl, benzyloxycarbonyl, methoxycarbonyl, ethoxycarbonyl, n-propoxycarbonyl and isopropoxycarbonyl,
   said acid-binding agent is any one or more of sodium hydroxide, potassium hydroxide, potassium carbonate, sodium carbonate, triethylamine and N-methylmorpholine;

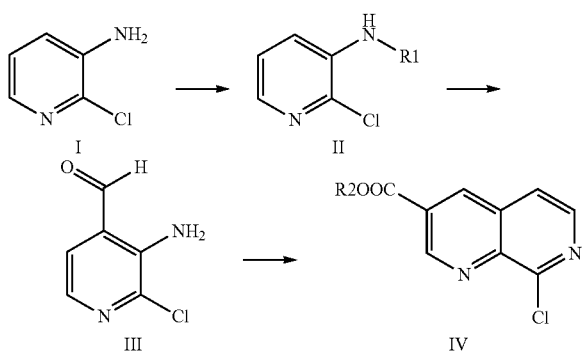

(2) said Compound II is reacted with an aldehydation reagent under alkaline conditions to make Compound III,
   wherein said aldehydation reagent is added dropwise, the temperature is ~100~10° C., the molar ratio of said Compound II, said alkali, said tetramethylethylene diamine and said aldehydation reagent is 1.0:1.0~5.0:1.0~5.0:1.0~5.0,
   said alkali is any one or more of n-butyl lithium, tert-butyl lithium, lithium diisopropylamide, and lithium hexamethyldisilazide,
   said solvent is any one or more of tetrahydrofuran, methyltetrahydrofuran, dioxane, and methyl tert-butyl ether,
   said aldehydation reagent is any one or more of dimethylformamide, diethylformamide, and N-formylmorpholine;
   (3) said Compound III is cyclized with acrylate compounds make Compound IV with a Lewis acid,
   wherein said Compound III, said Lewis acid and said acrylate compounds are dissolved in a solvent, and the temperature is 10~120° C.,
   said solvent is any one or more of ethyl acetate, isopropyl acetate, acetonitrile, tetrahydrofuran, methyltetrahydrofuran, dioxane and methyl tert-butyl ether,
   said Lewis acid is any one or more of sodium tetrafluoroborate, lithium tetrafluoroborate, calcium tetrafluoroborate and potassium tetrafluoroborate,
   said acrylate compounds are N,N-dimethylamino ethyl acrylate, N,N-dimethylamino acrylate, N,N-dimethylamino propyl acrylate and N,N-dimethylamino butyl acrylate,
   the molar ratio of said Compound III, said Lewis acid and said acrylate compounds is 1.0:0.5~10:1.0~5.0,
   R2 in said Compound IV is any one of a hydrogen atom, a methyl group, an ethyl group, a propyl group, an isopropyl group, a butyl group, an isobutyl group and a tert-butyl group.

2. The method for synthesizing 1,7-naphthyridine derivatives according to claim 1, wherein in step (1), the reaction temperature is 60~100° C.

3. The method for synthesizing 1,7-naphthyridine derivatives according to claim 1, wherein in step (1), said protecting group reagent is any one or more of tert-butyl chloroformate, isobutyl chloroformate, di-tert-butyl dicarbonate and diisobutyl decarbonate.

4. The method for synthesizing 1,7-naphthyridine derivatives according to claim 1, wherein in step (1), said solvent is any one or more of toluene, tetrahydrofuran, methyltetrahydrofuran, dioxane, methyl tert-butyl ether and n-heptane.

5. The method for synthesizing 1,7-naphthyridine derivatives according to claim 1, wherein in step (1), said acid-binding agent is potassium carbonate, sodium carbonate and triethylamine.

6. The method for synthesizing 1,7-naphthyridine derivatives according to claim 1, wherein in step (1), said molar ratio of said Compound I, said protecting group reagent and said acid-binding agent is 1.0:1.0~2.0:0~3.0.

7. The method for synthesizing 1,7-naphthyridine derivatives according to claim 1, wherein in step (2), after said Compound II, said alkali, said tetramethylethylene diamine and said solvent are reacted at −20~−40° C., said aldehydation reagent is added dropwise, and an aldehydation reaction is carried out at −20~−40° C., said Compound III is obtained.

8. The method for synthesizing 1,7-naphthyridine derivatives according to claim 1, wherein in step (2), said alkali is n-butyl lithium, said solvent is tetrahydrofuran, said aldehydation reagent is N-formylmorpholine, said molar ratio of said Compound II, said alkali, said tetramethylethylene diamine and said aldehydation reagent is 1.0:2.0~3.0:1.0~2.0:1.0~2.0.

9. The method for synthesizing 1,7-naphthyridine derivatives according to claim 1, wherein in step (3), said Compound III, said Lewis acid and said acrylate compounds are dissolved in a solvent, and a cyclization reaction occurs at 50~80° C. to prepare said Compound IV.

10. The method for synthesizing 1,7-naphthyridine derivatives according to claim 1, wherein in step (3), said solvent is acetonitrile, said Lewis acid is lithium tetrafluoroborate, said acrylate compounds are N,N-dimethylamino ethyl acrylate, said molar ratio of said Compound III, said Lewis acid and said acrylate compounds is 1.0:1.0~2.0:1.5~3.0, R2 in said Compound IV is an ethyl group.

11. The method for synthesizing 1,7-naphthyridine derivatives according to claim 1, wherein in step (3), the molar ratio of said Compound III, said Lewis acid and said acrylate compounds is 1.0:1.0~2.0:1.5~3.0.

12. The method for synthesizing 1,7-naphthyridine derivatives according to claim 3, wherein in step (1), said protecting group reagent is tert-Butoxycarbonyl and isobutoxycarbonyl.

13. The method for synthesizing 1,7-naphthyridine derivatives according to claim 4, wherein in step (1), said solvent is methyltetrahydrofuran and/or dioxane.

* * * * *